United States Patent [19]

Albeck et al.

[11] Patent Number: 4,764,461

[45] Date of Patent: Aug. 16, 1988

[54] TELLURIUM AND SELENIUM COMPOUNDS FOR THE INDUCTION OF IN VIVO AND IN VITRO PRODUCTION OF CYTOKINES

[75] Inventors: Michael Albeck, Ramat Gan; Benjamin Sredni, Bnei Brak, both of Israel

[73] Assignee: Bar-Ilan University, Ramat-Gan, Israel

[21] Appl. No.: 57,800

[22] Filed: Jun. 3, 1987

Related U.S. Application Data

[60] Division of Ser. No. 782,129, Sep. 30, 1985, which is a continuation-in-part of Ser. No. 712,549, Mar. 15, 1985, abandoned, which is a continuation-in-part of Ser. No. 599,511, Apr. 12, 1984, abandoned.

[51] Int. Cl.$^4$ .................. C12P 21/00; C12N 5/02
[52] U.S. Cl. ............................ 435/68; 435/70; 435/948; 435/811; 435/240.25; 530/351; 424/85
[58] Field of Search ............ 435/68, 70, 240, 241, 435/948, 811; 530/351; 424/85

[56] References Cited

U.S. PATENT DOCUMENTS 4,239,846 12/1980 Gysling et al. .................. 430/202
4,508,662 4/1985 Schack et al. .................. 260/550

OTHER PUBLICATIONS

Kay et al, *IRCS Med. Sci*, vol. 14(7) 1986, pp. 691–692.
Kaller et al, *Clin. Exp. Immunol.*, 63(3) 1986, pp. 570–576.
Mayberry et al., *J. Leukocyte Biol.*, 39(4) 447–56, 1986.
Aziz et al., *Vet Immunol Immunopathol*, 10(4) 1985, pp. 381–90.
Bradt et al., Proc. of Academy of Science, p. 72.
J.A.C.S., 103, 2340–2347 (1981).
Naturfosch 36b, 307–312 (1981).

*Primary Examiner*—John Kight
*Assistant Examiner*—Garnette D. Draper
*Attorney, Agent, or Firm*—Hedman, Gibson, Costigan & Hoare

[57] ABSTRACT

Certain tellurium compounds have been found to have the ability to stimulate the in vivo and in vitro production of cytokines and their receptors. These compounds may be utilized in the treatment of certain tumors, autoimmune diseases, immune diseases and infectious diseases.

7 Claims, 2 Drawing Sheets

TELLURIUM AND SELENIUM COMPOUNDS FOR THE INDUCTION OF IN VIVO AND IN VITRO PRODUCTION OF CYTOKINES

This is a divisional of U.S. application Ser. No. 782,129, filed Sept. 30, 1985, which is a continuation-in-part of application U.S. Ser. No. 712,549, filed Mar. 15, 1985, now abandoned, which in turn is a continuation-in-part application of U.S. Ser. No. 599,511, filed Apr. 12, 1984, now abandoned.

BACKGROUND OF THE INVENTION

It is well known that the growth of normal lymphocytes is dependent not only on contact with an antigenic substance or a mitogen, but also on the presence of certain growth factors known as lymphokines. One of these growth factors is known as T-cell growth factor (TCGF) better known as interleukin-2 (IL-2). The discovery of this growth factor (Gillis, et al., Nature, 268; 154 (1977) and Ruscetti, et al., J. Immunol, 119; 131 (1977)) resulted in the large scale growth and cloning of T-lymphocytes as sources for IL-2.

The lymphocytes or white blood cells in the animal body come in two types, B-cells and T-cells. The B-cells produce antibodies in the form of immunoglobulins that bind onto invading organisms while the T-cells produce the lymphokines which are responsible for turning B-cells on or off. See for example Cell. Immunol. 36: 15 (1978); J. Cell Physiol. 96: 53 (1978); Eur. J. Immunol. 8: 681 (1978); Immunol. Rev. 54: 188 (1981); Immunol. Rev. 54: 158 (1981); J. Exp. Med. 154: 1500 (1981); National Cancer Institute Mon. 60: 211 (1982); Int. J. Cancer 28: 157 (1981); The Potential Role of T-Cell Subpopulations in Cancer Therapy, Eds. A. Fefer & A. Goldstein, Raven Press, N.Y. pp 173 et seq. (1982); J. Immunol, 128: (258) 1982.

The known types of lymphokines include, in addition to IL-2, B-cell factors, macrophage activation factor (MAF), Interleukin-3 (IL-3), Colony Stimulating Factor (CFS), Tumor Necrosis Factor, and other factors produced by monocytes such as Interleukin-1 (IL-1) and Gamma Interferon. All of these factors are secreted by white blood cells and are collectively known as cytokines. Great attention has been given to using various recombinant DNA techniques and other methodologies for cloning normal T and B cell lines that can produce these materials. See for example Nature 259: 130 (1976); Immunology 32: 319 (1977); Exp. Hemat, 8: 494 (1980); Nature 283: 581 (1980); Proc. Natl. Acad. Sci. U.S.A. 78: 1858 (1981); J. Immunol. Methods 49: 1 (1982); Nature 29424/31: 697–699 (1981), all of which are incorporated by reference.

The present invention is based on the discovery of a class of synthetic organic derivatives of tellurium or selenium that are capable of stimulating cytokine producing cells to produce significant quantities of cytokines both in vivo and in vitro. This discovery makes possible a novel therapeutic approach in the treatment of cancer, immune deficiencies, autoimmune diseases and infectious diseases.

Accordingly, it is an object of the invention to provide novel compounds based on tellurium or selenium that are useful as therapeutic agents.

It is also an object of the invention to provide a novel method for producing in vitro cytokines such as lymphokines and induce receptors to these cytokines.

It is also an object of the invention to produce in vivo cytokines such as lymphokines and induce receptors to cytokines for the treatment of diseases such as cancer, immune deficiencies, autoimmune diseases and infectious diseases.

It is also an object of the invention to provide novel pharmaceutical compositions that are based on tellurium compounds that produce cytokines in vivo and in vitro.

SUMMARY OF THE INVENTION

Figure 1:
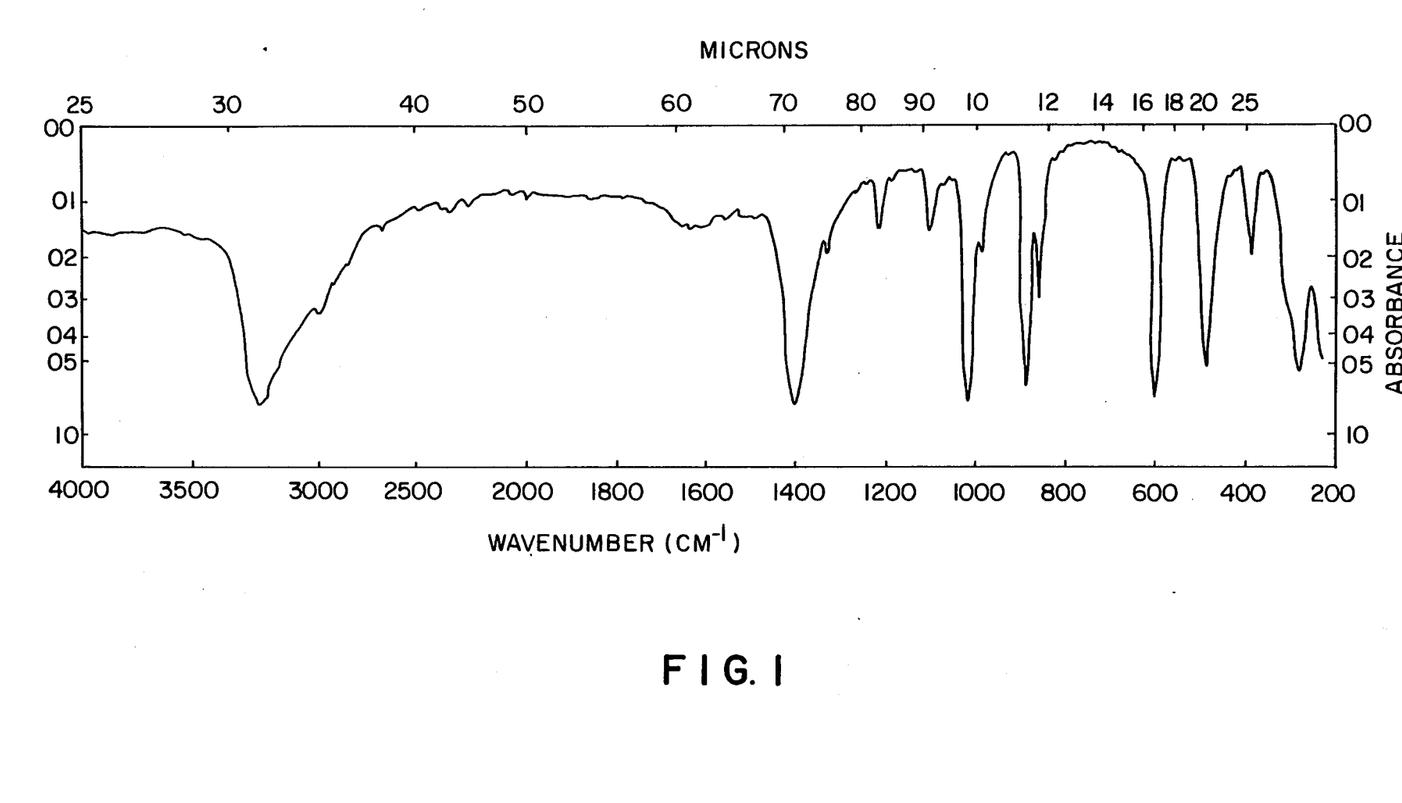
FIG. 1 is an infrared analysis of the compound of Example 1 in KBr.
Figure 2:
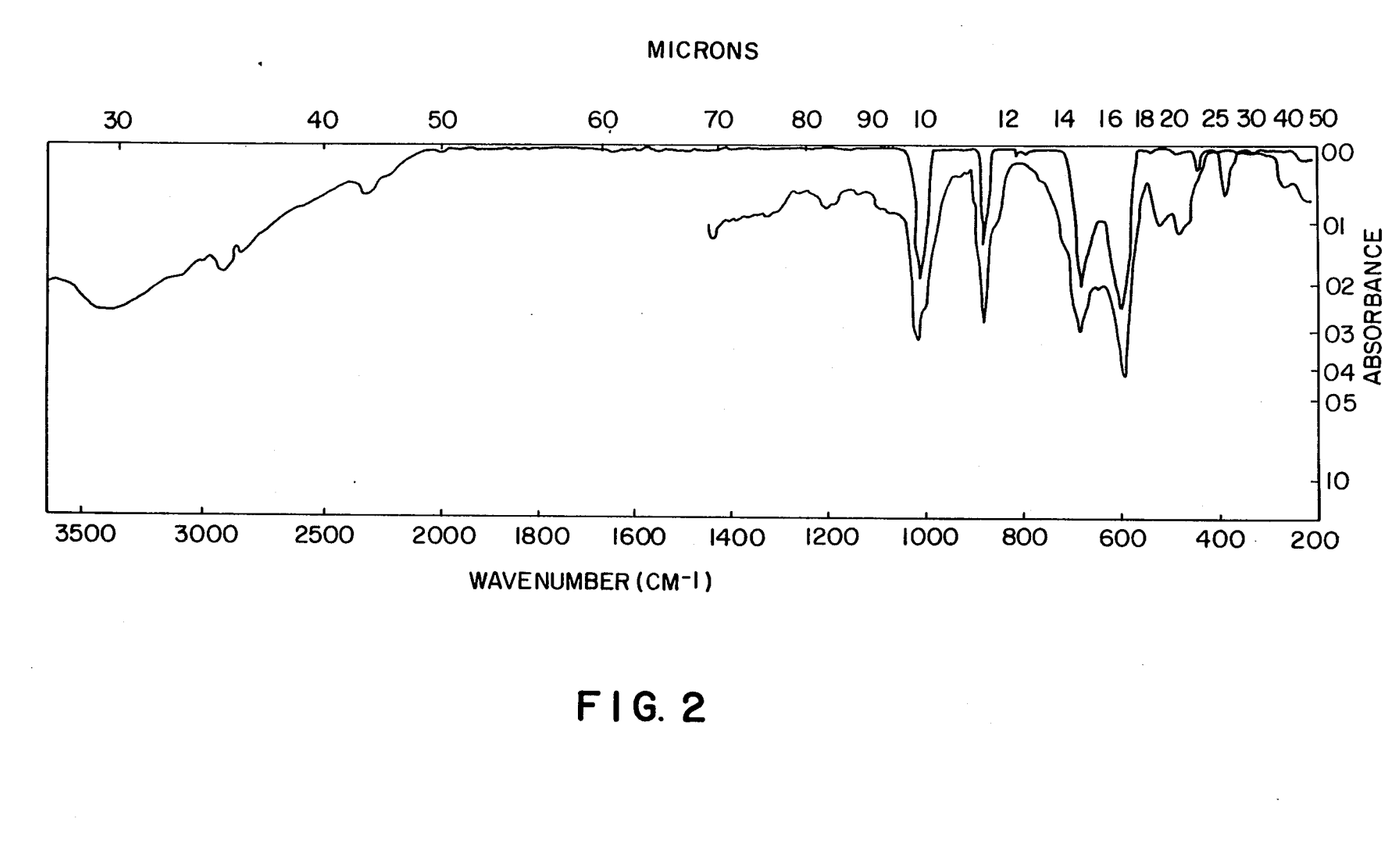
FIG. 2 is an infrared analysis of the compound of Example 2 in KBr.

The derivatives of tellurium or selenium that are useful in the present invention include those compounds of the following general formulas which stimulate cells to produce lymphokines:

(A)

or (B)

or

TeO$_2$ (C)

or

PhTeCl$_3$ (D)

or $(C_6H_5)^+ P(TeCl_3(O_2C_2H_4))^-$ (E)

wherein Q is Te or Se; t is 1 or O; u is 1 or O; v is 1 or O; R, R$_1$, R$_2$, R$_3$, R$_4$, R$_5$, R$_6$, R$_7$, R$_8$ and R$_9$ are the same or different and are independently selected from the group consisting of hydrogen, hydroxyalkyl of 1 to 5 carbons, hydroxy, alkyl of from 1 to 5 carbon atoms, halogen, haloalkyl of 1 to 5 carbon atoms, carboxy, alkylcarbonylalkyl of 2 to 10 carbons, alkanoyloxy of 1 to 5 carbon atoms, carboxyalkyl of 1 to 5 carbon atoms, acyl, amido, cyano, amidoalkyl of 1 to 5 carbons, N-monoalkylamidoalkyl of 2 to 10 carbons, N,N-dialkylamidoalkyl of 4 to 10 carbons, cyanoalkyl of 1 to 5 carbons, alkoxy of 1 to 5 carbon atoms, alkoxyalkyl of 2 to 10 carbon atoms and —COR$_{10}$ wherein R$_{10}$ is alkyl of from 1 to 5 carbons; and X is halogen; while the ammonium salt is illustrated, it is understood that other pharmaceutically acceptable salts are within the scope of the invention. The compounds with the five membered rings are preferred.

As used herein and in the appended claims, the term alkyl of 1 to 5 carbon atoms includes straight and branched chain alkyl groups such as methyl; ethyl; n-propyl; n-butyl, and the like; the term hydroxyalkyl of 1 to 5 carbon atoms includes hydroxymethyl; hydroxyethyl; hydroxy-n-butyl; the term haloalkyl of 1 to 5 carbon atoms includes chloromethyl; 2-iodoethyl; 4-bromo-n-butyl iodoethyl; 4-bromo-n-pentyl and the like; the term alkanoyloxy of 1 to 5 carbon atoms includes acetyl, propionyl, butanoyl and the like; the term carboxyalkyl includes carboxymethyl, carboxyethyl, ethylenecarboxy and the like; the term alkylcarbonylalkyl includes methanoylmethyl, ethanoylethyl and the like; the term amidoalkyl includes —$CH_2CONH_2$; —$CH_2CH_2CONH_2$; —$CH_2CH_2CH_2CONH_2$ and the like; the term cyanoalkyl includes —$CH_2CN$; —$CH_2CH_2CN$; —$CH_2CH_2CH_2CN$ and the like; the term alkoxy of 1 to 5 carbon atoms includes methoxy, ethoxy, n-propoxy, n-pentoxy and the like; the terms halo and halogen are used to signify chloro, bromo, iodo and fluoro; the term acyl includes $R_{16}CO$ wherein $R_{16}$ is H, or alkyl of 1 to 5 carbons such as methanoyl, ethanoyl and the like; the term aryl includes phenyl, alkylphenyl and naphthyl; the term N-monoalkylamidoalkyl includes —$CH_2CH_2CONHCH_3$, —$CH_2CONHCH_2CH_3$; the term N,N-dialkylamidoalkyl includes —$CH_2CON(CH_3)_2$; $CH_2CH_2CON(CH_2CH_3)$. Compounds which are based on tellurium are the presently preferred compounds of the invention. The tellurium based compounds that are preferred include those of the formula:

and wherein X is halogen. The preferred halogen species is chloro. These compounds are capable of inducing IL-2 formation as well as the proliferation of IL-2 producer cells and the activation of IL-2 receptor sites.

Other compounds which are based on tellurium and may be used in the practice of the invention include $PhTeCl_3$, $TeO_2$ and $(C_6H_5)_4P^+(TeCl_3(O_2C_2H_4)^-$ (Z. Naturforsh, 36B, 307–312 (1981). The compound hereinafter described in Example 2 has the following structure:

Other compounds useful for the practice of invention include:

Wherein $R_{11}$, $R_{12}$, $R_{13}$ and $R_{14}$ are independently selected from the group consisting of hydrogen, hydroxyalkyl of 1–5 carbon atoms, hydroxy and alkyl of 1–5 carbon atoms.

Useful dihydroxy compounds for use in the preparation of compounds of structure A or B, include those of formula I wherein R, $R_1$, $R_4$ and $R_5$ are as shown in the Table:

TABLE $$\begin{array}{c} R \quad R_4 \\ | \quad | \\ HO-C-C-OH \\ | \quad | \\ R_1 \quad R_5 \end{array} \quad (I)$$

| R | $R_1$ | $R_4$ | $R_5$ |
|---|---|---|---|
| H | H | H | H |
| H | Cl | H | H |
| H | $OCH_3$ | H | H |
| H | $COOCH_3$ | H | H |
| H | H | CN | H |
| H | CHO | H | H |
| H | H | COOH | H |
| H | CHCOOCH | H | H |
| H | H | $CHCOOCH_3$ | H |
| H | I | H | H |
| H | H | Br | H |
| H | H | $CONH_2$ | H |
| H | H | $CH_2OH$ | H |
| H | COOH | H | H |

Other dihydroxy compounds for use in the preparation of compounds A and B include those of formula II wherein R, $R_1$, $R_2$, $R_3$, $R_4$ and $R_5$ are as shown in the Table:

$$\begin{array}{c} R \quad R_2 \quad R_4 \\ | \quad | \quad | \\ HO-C-C-C-OH \\ | \quad | \quad | \\ R_1 \quad R_3 \quad R_5 \end{array} \quad (II)$$

| R | $R_1$ | $R_2$ | $R_3$ | $R_4$ | $R_5$ |
|---|---|---|---|---|---|
| H | H | H | H | H | H |
| H | H | Cl | H | H | H |
| H | $CH_2OH$ | H | H | H | H |
| H | H | OH | H | H | H |
| H | H | H | $CH_3$ | H | H |
| H | H | H | $CH_2Cl$ | H | H |
| H | H | H | COOH | H | H |
| H | H | H | $CH_2COOH$ | H | H |
| H | H | H | CHO | H | H |
| H | H | H | H | H | $CH_2CHO$ |
| H | H | $CONH_2$ | H | $H_2$ | $CH_3$ |
| H | H | H | CN | H | H |
| H | H | H | H | $CH_2CONH_2$ | H |
| H | H | H | $COOCH_3$ | $H_3$ | H |
| H | $H_3$ | $OCH_3$ | H | H | H |

Other dihydroxy compounds for use in making compound formula A and B include those of formula III wherein R, $R_1$, $R_2$, $R_3$, $R_4$ and $R_5$ are as shown in the Table.

(III)

| R | R$_1$ | R$_2$ | R$_3$ | R$_4$ | R$_5$ | R$_8$ | R$_9$ |
|---|---|---|---|---|---|---|---|
| H | H | H | H | H | H | H | H |
| H | H | Cl | H | H | H | H | H |
| H | H | H | H | Br | H | H | H |
| H | H | OCH$_3$ | H | H | H | H | H |
| H | H | CONH$_2$ | H | H | H | H | H |
| H | Br | H | H | Br | H | H | H |
| H | H | H | H | CH$_2$COOH | H | H | H |
| H | H | Cl | Cl | H | H | H | H |
| H | CH$_2$COOH | H | H | H | H | H | H |
| H | H | CH$_3$ | H | H | H | H | H |
| H | CH$_3$ | H | H | H | H | H | H |
| H | CH$_2$Cl | H | H | H | H | H | H |
| H | H | H | H | I | H | H | H |
| H | CH$_2$CN | H | H | H | H | H | H |
| H | H | H | H | CH$_2$CH$_2$OH | H | H | H |

Additional dihydroxy compounds include those of formula IV wherein R, R$_1$, R$_2$, R$_3$, R$_4$ and R$_5$ are as shown in the Table.

(IV)

| R | R$_1$ | R$_2$ | R$_3$ | R$_4$ | R$_5$ | R$_6$ | R$_7$ | R$_8$ | R$_9$ |
|---|---|---|---|---|---|---|---|---|---|
| H | H | H | H | H | H | H | H | H | H |
| H | H | Cl | H | H | H | Cl | H | H | H |
| H | H | Cl | Cl | H | H | H | H | H | H |
| H | H | CONCH$_3$ | H | H | H | Br | H | H | H |
| H | H | Br | H | H | H | CON(CH$_3$)$_2$ | H | H | H |
| H | H | H | OCH$_3$ | H | H | H | H | H | H |
| H | H | H | H | OCH$_3$ | H | H | H | H | H |
| H | H | H | H | CH$_2$COOH | H | H | H | H | H |
| H | H | COOH | H | H | H | H | H | H | H |
| H | CH$_3$ | H | H | H | H | H | H | H | H |
| CH$_3$ | H | H | H | H | CH$_3$ | H | H | H | H |
| H | CH$_2$CH$_3$ | H | H | H | H | H | Cl | H | H |
| H | CH$_2$CN | H | H | CH$_2$OH | H | H | H | H | H |
| H | H | H | I | H | H | H | H | CN | H |
| H | CH$_2$CH$_2$COOH | H | H | H | H | H | H | H | H |
| H | H | H | CHO | H | H | H | H | H | H |
| H | H | H | F | H | H | H | H | H | H |

The compounds of the formula:

wherein R$_{11}$, R$_{12}$ and R$_{15}$ are as defined hereinabove; may be made by reacting the appropriate di, tri or tetrahaloselenide or telluride with the appropriate hydroxy compound which may be of the formula:

HO—R$_{16}$

R$_{16}$ is alkyl of 1 to 5 carbons, haloalkyl of 1 to 5 carbons, aryl, alkylaryl, alkylamido of 1 to 5 carbons, alkylcarbonyl of 1 to 5 carbons, cyanoalkyl of 1 to 5 carbons, cyanoalkyl of 1 to 5 carbons, and an alkoxyalkyl of 2 to 10 carbons. Specific examples of R$_{16}$ include methyl, ethyl, n-propyl, phenyl, tolyl, amidoethyl, cyanomethyl, methyloxymethyl and CH$_2$CH$_2$COOH.

The compounds are made by combining substantially equimolar amounts of the reactants in a suitable reactor at room temperature or at elevated temperatures up to the reflux temperature. It is preferred to utilize a solvent that is capable of dissolving the reactants such as acetonitrile, benzene, toluene, xylene, dimethylsulfoxide, mixtures thereof and the like. Compounds of structure (A) are only obtained in acetonitrile. The preferred method requires heating the reaction mixture to the reflux temperature of the solvent while stirring the reaction mixture with a suitable magnetic or mechanical stirrer. The reaction may be carried out for a sufficient period of time to ensure complete reaction of the reactants. This time will vary with the reaction conditions, the particular compound being made and the nature of the solvents. The reaction may be run at atmospheric pressure but if desired may be carried out at reduced or elevated pressure. The reaction is practically carried out in the presence of an oxygen containing atmosphere such as air but inert atmospheres such as nitrogen, argon, helium or mixtures thereof may be utilized if desired. Reaction times of 1 minute to 168 hours may be used although reaction times of 6–16 hours are preferred.

The reactor should be of glass construction or lined with glass or other ceramic material that is inert with respect to the reactants.

Usually the compounds produced in the process will precipitate as the reaction mixture is cooled to room temperature. Precipitation may also be effected by adding a suitable precipitant such as a liquid alkane such as hexane or by concentration of the reaction mixture by solvent removal by evaporation with or without the aid of vacuum. The product may be collected in a sintered glass filter, washed with a cold solvent and dried using conventional techniques. The product is stored in a suitable container, protected from light, and preferably at reduced temperature to avoid decomposition.

The solvent system for administration of the compounds of the invention may be based on dimethylsulfoxide or lower alkanols such as ethanol and propanol, glycols such as ethylene glycol, glycerol, propylene glycol and the like. The preferred solvent system is a phosphate buffered saline solution which contains an mechanical agitation for an extended period of time which will dissolve the compound. Generally ultrasound is produced by a transformer which transforms 50/60 hertz, line voltage AC into high frequency electrical energy which is coupled to a transducer. By using piezoelectric ceramics, electrical frequency is converted into mechanical vibration. Typical amplitudes of 0.0003 for 40 k Hz equipment and 0.00007 to 0.001 for 20 k Hz equipment are useful. The transducer may be provided with a booster that is connected to a horn that has means for conducting the ultrasound to a container that holds the liquid for dissolving the compounds of the invention. Useful devices include small scale ultrasonic cleaners such as the Bronson instrument. It has been found that solutions containing about 5 mg/100 ml of the compound of the invention may be prepared by applying ultrasound for a sufficient period of time to provide an aqueous liquid containing the compound. The time required for this is usually 3 hours to 24 hours. High speed mechanical shakers such as a Tutenhauer shaker or waring blenders may be used for this purpose. The use of an electically operated agitator will cause the compounds to form a solution or dispersion after about 3 to 4 hours of agitation.

It has been discovered that glycerol may be used in the preparation of aqueous liquids that contain the compound. These preparations are then diluted with an aqueous injectable diluent such as water, saline solution etc. The preferred diluent is PBS.

DESCRIPTION OF THE PREFERRED EMBODIMENTS

The following examples are given to illustrate the invention and it is understood that they do not limit the scope of the invention.

EXAMPLE 1

0.01 mol of ethylene glycol and 0.01 mol of tellurium tetrachloride were dissolved in 35 ml of dry acetonitrile and placed in a flask fitted with a reflux condenser and a magnetic stirrer. The reaction mixture was refluxed for six hours. The solution was filtered while hot through a sintered glass filter. The filtrate was collected and allowed to reach room temperature which resulted in the formation of a white precipitate. The precipitate was filtered and collected on a sintered glass filter and washed with cold acetonitrile. It was dried for 10 hours under vacuum of 0.05 mm/Hg. The mp(d) was ca. 200° C. The calculated elemental analysis was %C=7.70; H=2.57; N=4.49; Cl=34.06; O=10.26; Te=40.92; found, C=7.87; H=2.5; N=4.5; Cl=33.38; O=10.13; Te=41.12. The P.M.R. spectra (deuterated DMF)$\delta$(ppm): 4.43(4H, S); 7.7(4H, t); The mass spec. was m/e: 130, 160, 165, 180, 190, 200, 222, 224, 247, 251, 258, 260; the 13C NMR spectrum confirms the presence of $CH_2$ groups; the $^{125}Te$ NMR spectrum confirms the presence of one Te atom in the molecule.

The difference in the Cl analysis may be due to the presence of a small quantity of the compounds of formula II in the sample.

EXAMPLE 2

0.01 mol of ethylene glycol was added to 0.01 mol of tellurium tetrachloride in 50 ml of dry benzene in flask fitted with a reflux condenser and a magnetic stirrer. The reaction mixture was refluxed for 16 hours and filtered while hot through a sintered glass filter and worked up as in Example 1 using benzene as a wash liquid to give the compound of formula II. The mp(d) was ca. 250° C.

EXAMPLE 3

A solution of the compound of Example 1 was prepared as follows: 5 mg was placed in a volumetric flask to which was added 100 ml of a solution of 40% dimethyl sulfoxide (DMSO) and 60% phosphate buffer saline (PBS) solution resulting in a concentration of 10 $\mu$g/0.2 ml. If the solution becomes turbid, it is centrifuged at 2000 rpm for ten minutes and the clear supernatant portion is used.

The test animals were Balb-c, male, mice, 6 to 8 weeks of age. All injections were made intraperitoneally using 0.2 ml of the solution of the compound of Example 1 using 25 gauge 5/8" hypodermic needle.

The animals received the following injections:
 (a) Control (no injection)
 (b) Control (0.2 ml DMSO)
 (c) 1 $\mu$g of compound of Example 1 (in 0.2 ml DMSO/PBS solution)
 (d) 10 $\mu$g of compound of Example 1 (in 0.2 ml of DMSO/PBS solution)

Each of groups a, b, c and d consisted of 21 animals. The animals were sacrificed daily from 24 h to 7 days after injection.

On each day, spleen cells from three of the animals from each control group were pooled together and processed by passing the spleen cells through a 60 mesh stainless steel net in a 5 mm Petri dish containing PBS in order to separate the cells. The cells were collected and centrifuged at 1000 rpm for 10 minutes. The supernatant was discarded and the cells were treated for two minutes with 5 ml of hypotonic buffer (0.15M $NH_4CL$, 0.01M $KHCO_3$ dissolved in double distilled water, pH 7.2) to kill the erythrocytes. Thereafter, PBS was added to the cells and the cells were centrifuged for 10 minutes at 1000 rpm. The cells were washed twice with PBS and counted in a haemocytometer using trypan blue to test for viability. The cells were brought to a concentration of $10^7$ cells/ml using enriched RPMI containing 10% fetal calf serum (Ser Lab, Sussex, England); $5 \times 10^{-5}M$ 2-mercaptoethanol and 3% of d-glutamine (Bio Lab Israel) (stock solution 2 mM$\times$1000 nonessential amino acids) (Bio Lab, Israel) (stock solution$\times$100) and sodium pyruvate (Bio Lab, Israel) (stock solution 1 mM$\times$100).

An additional three animals from each of the experimental groups were sacrificed and each of the spleens was processed separately using the same procedure.

The cell mixture was divided into two groups.

(a) Cells at a concentration of $10^7$ cells/ml enriched RPMI to which was added concanavalin-A (CON A) (DiFCO, Batch 352) 2 $\mu$g./ml. These cells were incubated in 5 mm Petri dishes (NUNC) for 24 hours at 37° C., 7.5% $CO_2$. Supernatants were collected, centrifuged at 1,600 rpm for 10 minutes and stored at 4° C. until used. These supernatants were assayed for IL-2 and CSF activity.

(b) Cells at a concentration of $10^7$ cells/ml enriched RPMI which were incubated at 37° C., 7.5% $CO_2$ for 96 h., without addition of CON A. Supernatants were collected, centrifuged and stored at 4° C. until used. These supernatants were assayed for CSF activity.

Prior to incubation of the cells, samples were removed from culture plates and smears of the cultures were made by cytocentrifugation. Slides were stained with May-Grunwald-Giemsa (1:10) solution and evaluated morphologically. A radioactive thymidine assay was used to determine IL-2 activity.

ASSAY FOR IL-2 ACTIVITY

1. Supernatants were tested for IL-2 activity by the proliferation of the IL-2 dependent cell line CTLD. The IL-2 assay is based on the growth dependence of these cultured T-cell lines on IL-2. T cells harvested from IL-2 dependent culture, washed and placed back in culture in the absence of IL-2 invariably die within 24 hr. By using tritiated thymidine incorporation ($^3$H-TdR) as an index of cultured T-cell replication, the IL-2 microassay provides a highly reproducible and quantitive indication of the amount of IL-2 activity in the supernatant prepared hereinabove.

2. To assay a condition medium for IL-2 activity, a sample containing $5 \times 10^4$ CTLD cells, 10% fetal calf serum and 50% of supernatant in question, all were suspended in a final volume of 1 ml RPMI. Aliquots of 0.2 ml from each sample were placed in four replicate wells of 96 microwell tissue culture plates (NUNC). Conditioned medium was obtained from cultures of Charles River rat spleen cells stimulated with Con A that contained a known amount of IL-2 as a reference in all assays.

3. The microwells were incubated for 24 hr at 37 degrees C. after which 1 microcurie/well of $^3$H-methylthymidine was added. Cells were then further incubated overnight, harvested with a cell harvester, and counted in a beta scintillator.

The results, in counts per minute (CPM) were as follows and indicate the relative quantity of IL-2 that is present in the supernatants.

(a) Control (no injection)
(b) Control (0.2 ml DMSO)
(c) 1 μg of compound of Example 1 (in 0.2 ml DMSO/PBS solution)
(d) 10 μg of compound of Example 1 (in 0.2 ml of DMSO/PBS solution)

|      | day 1  | day 2  | day 3  | day 4  | day 6  | day 7  |
|------|--------|--------|--------|--------|--------|--------|
| (a)* | 37,695 | 32,055 | 24,758 | 45,029 | 25,065 | 36,775 |
| (b)* | 16,323 | 30,824 | 24,861 | 30,555 | 48,921 | 38,626 |
| (c)  | 25,919 | 21,398 | 10,130 | 31,999 | 41,261 | 66,854 |
| (c)  | 34,326 | 22,050 | 13,235 | 14,226 | 80,314 | 58,094 |
| (c)  | 16,718 | 9,338  | 2,176  | 17,228 | 42,485 | 51,268 |
| (d)  | 24,335 | 31,901 | 20,316 | 26,644 | 22,040 | 85,216 |
| (d)  | 21,193 | 36,390 | 18,288 | 18,051 | 74,043 | 6,299  |
| (d)  | 25,381 | 22,066 | 12,126 | 65,963 | 43,838 | —      |

*spleens from control animals were pooled after removal from animal.

EXAMPLE 4

This example describes the stimulation of IL-2 production from human mononuclear cells by the use of the compound of Example 1.

Venous whole blood (with heparin, Evans: 10 IU/ml blood) was diluted with RPMI in a ratio of 1:1. The diluted blood was gently placed on Lymphoprep (Nylgard & Co., Oslo, Norway, density 1.077 g/ml) two parts of diluted blood on one part of Lymphoprep. Each tube was provided with 3 ml Lymphoprep and 6 to 7 ml diluted blood. The tubes were centrifuged 30 minutes at 1600 rpm at room temperature. After the centrifugation, mononuclear cells were collected from the interphase fraction and washed with RPMI three times. The cells were resuspended in RPMI, counted on a hemocytometer, using trypan blue to test for viability and brought to a concentration of $1 \times 10^{-6}$ cells per ml in enriched RPMI. Varying concentrations of the compound of Example 1 ranging from 50 μg/ml to 5 pg/ml were added in a volume of 10% of cell mixture. Aliquots of 0.2 ml from each sample were placed in wells of microplates (NUNC) (triplicates). The microplates were incubated for 72 hours at 37° C. after which $^3$H-methylthymidine, 1 u Ci/well (Nuclear Research Center, Israel) was added to the cultures. Cells were further incubated overnight and harvested with a cell harvester. Proliferation of human mononuclear cells was increased by 5 to 6 fold in the range of 1 to 10 ng/ml of cells of the compound of Example 1 thus suggesting that the compound of Example 1 either induced the production of IL-2 in a subset of the mononuclear cells resulting in the observed proliferation and/or the induced receptor formation in a given population which would also result in proliferation.

EXAMPLE 5

This example illustrates the in vivo effect of the compound of Example 1 on an experimentally induced tumor.

A solution of 0.2% of methylcholanthrene (MCA, Sigma, USA) was prepared by dissolving 2 mg of the carcinogen in 1.0 ml of olive oil (Ref: Petra, et al., Cancer 19: 302, 1961) with continuous shaking at 37° C. for 30 minutes. Six to eight week old C$_3$Heb mice were injected with 0.6 mg MCA/0.3 ml of solvent/mouse subcutaneously in the rear right thigh.

After 21–30 days the induced tumor was surgically removed and pushed through 60 mesh stainless nets to obtain isolated cells. These cells were then further injected subcuteneously into the rear right thigh of C$_3$Heb mice 5 to 8 weeks of age, at a concentration of $10^6$ cells/0.3 ml PBS/mouse/hypodermic needle 25 gauge, ⅝" to further induce tumor formation.

Five days after injection of the tumor cells, a palpable tumor was induced. The animals were thereafter treated as follows:

(a) control (0.2 ml 40% DMSO 60% PBS, IP 1 day after the induced tumor was palpable)
(b) 10 μg of compound of Example 1, IP to 5 mice (in 0.2 ml 40% DMSO 60% PBS, 3 days after the induced tumor was palpable and a second injection of 10 ug of compound in the same solvent was administered 5 days after the first injection to 3 of the 5 mice.

The tumors were excised after 13 days and the volume was determined and is reported in the Table. All animals expired 35 to 38 days after the initial innoculation.

TABLE

| Group | Mouse | Compound of Ex. 1 Administration | Vol. of Tumor (13 days) |
|-------|-------|----------------------------------|--------------------------|
| a*    | 1     | —                                | 4.01                     |
| a*    | 2     | —                                | 3.7                      |
| a*    | 3     | —                                | 3.9                      |
| b     | 7     | day 3                            | 0.77                     |
| b     | 8     | day 3                            | 1.66                     |
| b     | 4     | day 3 and 5                      | 0.7                      |
| b     | 5     | day 3 and 5                      | 0.52                     |
| b     | 6     | day 3 and 5                      | 0.31                     |

*Control

EXAMPLE 6

Balb-c mice, age 7 weeks were injected with methylcholanthrene to induce the formation of fibrosarcoma cells according to the procedure of Example 5. The test animals were divided into two groups.

(a) control (0.2 IP of 40% DMSO and 60% PBS)
(b) 10 μg of compound of Example 1 (in 0.2 ml 40% DMSO 60% PBS, IP at intervals shown in Table 2)

TABLE 2

|     | Days After Inno- culation With Tumor Cells | Days after Injection With Compound Of Example 1 | % Survival |
|-----|---|---|---|
| (a)* | 24 | — | 100% |
|     | 25 | — | 63% |
|     | 34 | — | 55% |
|     | 46 | — | 45% |
|     | 60 | — | 35% |
|     | 67 | — | 18% |
|     | 69 | — | 0% |
| (b) | 4 | 4 | 100% |
|     | 9 | 9 | 100% |
|     | 23 | 23 | 100% |
|     | 30 | 30 | 100% |
|     | 37 | 37 | 100% |
|     | 39[1] | 39 | 100% |
|     | 41 | 41 | 100% |
|     | 43 | 43 | 100% |
|     | 46 | 46 | 80% |
|     | 48 | 48 | 80% |
|     | 50 | 50 | 80% |
|     | 53 | 53 | 60% |
|     | 60 | 60 | 40% |
|     | 67 | — | 20% |
|     | 68 | — | 0% |

*Control
[1]Day 39 marked the start of an increased dosage regimen to determine the toxicity of the compound of Example 1. The mortality results for group (b) were 0% until just after the increased dosage regimen.

EXAMPLE 7

This example describes the in vitro making of IL-2 and CSF from mouse spleen cells using the compound of Example 1 as the extrinsic stimulating agent.

Spleens were removed from 15, male Balb-c mice 6 to 8 weeks of age. The spleen cells were pushed through stainless steel 60 mesh (U.S. standard) nets resting in 5 mm Petri dishes containing PBS in order to separate the cells. The cells were then collected into centrifuge tubes and spun at 1000 rpm for 10 minutes. The supernatant was discarded and cells were treated with 5 ml of hypotonic buffer (0.15M NH$_4$Cl; 0.01M KHCO$_3$ dissolved in double distilled water, pH 7.2) for exactly two minutes. Thereafter, PBS was added to the cells and the test tubes were centrifuged for 10 minutes at 1000 rpm. The cells were rinsed twice and counted in a heamocytometer using trypan blue to test for viability. The cells were brought to a concentration of $10^7$ viable cells/ml. The cells were contacted with varying amounts of the compound of Example 1 in 1 ml of 40% DMSO 60% PBS. Table 3 shows the induction of IL-2 activity and colony stimulating factor that was obtained with varying amounts of the compound of Example 1.

TABLE 3

| Compound of Example 1 | IL-2 (cpm) | CSF (colonies/dish) |
|---|---|---|
| 50 μg | 5,000 | 2 |
| 5 μg | 5,000 | 5 |
| 500 ng | 5,000 | 25 |
| 50 ng | 6,000 | 75 |
| 5 ng | 15,000 | 120 |
| 500 pg | 30,000 | 175 |
| 50 pg | 38,000 | 260 |

TABLE 3-continued

| Compound of Example 1 IL-2 (cpm) | CSF (colonies/dish) |
|---|---|
| 5 pg    12,000 | 140 |

μg = micrograms
ng = nanograms
pg = picograms

Conrol animals injected with the DMSO solvent were found to have a IL-2 baseline of 4,000–5,000 CPM and a CSF of 70–80/colonies/dish.

EXAMPLE 8

Human mononuclear cells were obtained as described above and cultured for 72 hours at a concentration of $10^6$ cells/ml enriched RPMI, in the presence of varying concentrations of the compound of Example 1. Culture supernatants were collected, centrifuged and tested for IL-2 activity by using 50% of the volume of the supernatant assaying their ability to support the proliferation of the IL-2 dependent cell line CTLD. Table 4 reports the results of this assay.

TABLE 4

|     | Counts per minute |
|---|---|
| Compound of Example 1 | |
| 1 μg | 250 |
| 100 μg | 280 |
| 10 ng | 1,500 |
| 1 ng | 11,000 |
| Control: | |
| CTLD cells | 3,500 |

EXAMPLE 9

This example describes the stimulation of IL-2 production from human mononuclear cells by the use of the compound of Example 2.

Venous whole blood (with heparin, Evans: 10 IU/ml blood) was diluted with RPMI in a ratio of 1:1. The diluted blood was gently placed on Lymphoprep (Nylgard & Co., Oslo, Norway, density 1.077 g/ml) two parts of diluted blood on one part of Lymphoprep. Each tube was provided with 3 ml Lymphoprep and 6 to 7 ml diluted blood. The tubes were centrifuged 30 minutes at 1600 rpm at room temperature. After the centrifugation, mononuclear cells were collected from the interphase fraction and washed with RPMI three times. The cells were resuspended in RPMI, counted on a hemocytometer, using trypan blue to test for viability and brought to an enriched RPMI. Varying concentrations of the compound of Example 2 ranging from 50 μg/ml to 1 ng/ml were added in a volume of 10% of cell mixture. Aliquots of 0.2 ml from each sample were placed in triplicate wells of microplates (NUNC). The microplates were incubated for 72 hours at 37° C. after with $^3$H-methylthymidine, 1 u Ci/well (Nuclear Research Center, Israel) was added to the cultures. Cells were further incubated overnight and harvested with a cell harvester. Proliferation of human mononuclear cells was increased by 10 fold in the range of 1 to 10 ng of the compound of Example 2/ml cells thus suggesting that the compound of Example 2 either induced the production of IL-2 in a subset of the mononuclear cells resulting in the observed proliferation and/or the induced receptor formation in a given population which would also result in proliferation.

EXAMPLE 10

To a 100 ml solution of PBS* is added 5.0 mg of the compound of Example 1 using sterile conditions. The mixture is placed in a sonicator, and is sonicated for 4 hours. After the 4 hour period, the compound is dissolved to give a concentration of 10 μg/0.2 ml.

| *NaCl | 8.0 g |
|---|---|
| KCl | 200 mg |
| $Na_2HPO_4$ | 1150 mg |
| $KH_2PO_4$ | 200 mg |
| $CaCl_2$(anhyd.) | 100 mg/L |
| $MgCl_2 6H_2O$ | 100 mg/L |
| $H_2O$ | sufficient to make 1 liter |

EXAMPLE 11

Using 100 ml of the PBS of Example 10, 5.0 mg of the compound of Example 1 is dissolved by shaking in an electrically operated shaker for 4 hours, using sterile conditions to obtain a 10 μg/0.2 ml solution.

EXAMPLE 12

Using stirring 5.0 mg of the compound of Example 1 is dissolved under sterile conditions in 20 ml of glycerol. Thereafter 80 ml of PBS is added to form a solution containing 10 μg/0.2 ml.

It has been determined that the compound of Example 1 will dissolve as follows:
6.0 g/L in 40% glycerol/60% PBS
1.3 g/L in 20% glycerol/80% PBS
1.0 g/L in 10% glycerol/90% PBS

EXAMPLE 13

This example demonstrates the effect of oral administration of the compounds of Example 1 and 2 on the induction of lymphokines.

The compounds were administered to male Balb-C mice, 6-8 weeks of age by the administration of the compounds of Examples 1 and 2 in drinking water at a concentration of 10 μg/ml of water and 1 μg/ml of water for the compound of example 1 and 25 μg and 1 μg/ml of water for the compound of example 2. The water solution was prepared by dissolving the compounds in PBS at a concentration of 50 μg/ml PBS and diluting the resulting solution to the desired concentration. The compounds were administered over a 4 day period. The exact amount of liquid intake was recorded daily. After 4 days the mice were sacrificed and spleens removed and processed as described in Example 3. The cells were incubated at a concentration of $10^7$ cells/ml in enriched RPMI containing 2 μg/ml of con-A for 24 hours at 37° C. The supernatants were collected and tested for IL-2 content.

| Compound | ug/ml $H_2O$ | Intake/animal | cpm |
|---|---|---|---|
| Ex 1 | 10 μg/ml | 248 μg | |
| Ex 1 | 1 μg/ml | 23 μg | 49179 [+50%]* |
| Ex 2 | 25 μg/ml | 406 μg | 44500 [+35%]* |
| Ex 2 | 10 μg/ml | 123 μg | 36815 |
| Ex 2 | 1 μg/ml | 17 μg | 42500 [+30%]* |
| Control | | | 32843 |

*Percent increase as compared to control

The compound of Example 1 was thoroughly mixed with powdered sucrose and 10 μg of the compound of example 1 in 25 mg of powdered sucrose was placed in the mouth of each mouse.

After 24 hours the mice were sacrificed and the spleens were processed as described above. The IL-2 content was as follows:

| | cpm |
|---|---|
| Test 1 | |
| A | 250,175 [+117%]* |
| B | 166,475 [+50%]* |
| Control | 110,853 |
| Test 2 | |
| A | 55,382 [+69%]* |
| B | 41,938 [+28%]* |
| C | 29,172 [0] |
| Control | 32,980 |

*Calculated as percent increase as compared to control.

This experiment shows that the compound of example 1 is active for inducing lymphokine production when given in dry form or when hydrolyzed in an aqueous diluent.

EXAMPLE 14

Tellurium dioxide (0.5 mole) was suspended in 250 ml 1,2-ethanediol (excess) and the mixture was heated under reflux at 90° C. under a slight vacuum for 16 hours. A white crystalline product was obtained. The material was separated by filtration, dried and then purified by sublimation at 150° C. (0.25 mm Hg) mp 206°–210° C. Cf. JACS 103, 2340–2347 (1981) Anal. calc. for $C_4H_8O_4Te$: C, 19.2; H, 3.3; O, 25.07; Te 51.2. Found: C, 19.91; H, 3.12; O, 24.98; Te, 49.99. MS m/e 250. This compound has the following structure:

$$\begin{array}{c} H_2C-O \quad\quad O-CH_2 \\ | \quad\quad \diagdown Te \diagup \quad\quad | \\ H_2C-O \quad\quad O-CH_2 \end{array}$$

EXAMPLE 15

To a stirred solution of $TeCl_4$ (0.015 mol) and 1,2-propanediol (0.03 mol) in tetrahydrofuran (70 ml) at −40° C. was added dropwise triethylamine (0.06) in 30 ml of tetrahydrofuran. The white precipitate of triethylamine hydrochloride was removed by filtration. The filtrate was concentrated at room temperature and white oily crystals were obtained and purified by sublimation at 120° C. (0.25 mm Hg) M.S. m/e=204,278. This compound has the following structure:

$$\begin{array}{c} H_3C-CH-O \quad\quad O-CH-CH_3 \\ | \quad\quad \diagdown Te \diagup \quad\quad | \\ H_2C-O \quad\quad O-CH_2 \end{array}$$

EXAMPLE 16

Using the procedure of Example 1, the following compounds were made using tellurium tetrachloride and the corresponding diol:

(a)

(1,2-propane diol)
M.S.: 165;200; 239

(b)

2,3-butane diol
M.S.: 165;200;253

(c)

1,3-propane diol
M.S.: 165;200;239

(d)

1,4-butane diol

EXAMPLE 17

The compounds listed below were tested in vitro at various concentrations that ranged from 10 μg/ml cells to $1 \times 10^{-6}$ μg/ml of cell mixtures. Cells were obtained from spleens of male Balb/c mice 6–8 weeks of age. Spleens were pushed through a stainless steel 60 mesh strainer to separate cells. The erythrocytes were lysed by treatment with hypotonic buffer (0.15M NH4CL, 0.001M KHCO3 dissolved in double distilled water, pH 7.21 for two minutes. The remaining cells were rinsed twice and brought to a concentration of $10^7$ cells/ml enriched RPMI. The cells were then innoculated with the test compound and incubated for 24 hours at 37° C. in the presence of 7.5% CO2. The supernatants were collected thereafter and were tested for IL-2 activity by the proliferation of the IL-2 dependent cell line CTLD. These experiments showed that at 1 μg/ml of cell mixture most of the compounds exerted a maximum effect on IL-2 secretion.

| Compound | Spleen Cells (cpm) |
|---|---|
| Example 1 | 14,600 (+472%) |
| Example 14 | 10,300 (+304%) |
| Example 2 | 18,000 (+605%) |
| Ph2Te(OCOCH3)2* | 3,500 |
| Ph2TeCl2* | 2,300 |
| Ph2Te(OCOPh)2* | 4,300 |
| Ph2TeCl* | 2,100 |
| PhTeCl3 | 18,000 (+605%) |
| (pCH3OPh)2TeCl2 | 2,148 |
| Example 16(a) | 13,540 (+435%) |
| *no significant activity at level tested | |
| Example 16(b) | 10,650 (+318%) |
| Example 16(c) | 15,720 (+516%) |
| Example 16(d) | 18,075 (+608%) |
| TeO2 | 17,055 (+508%) |

-continued

| Compound | Spleen Cells (cpm) |
|---|---|
| Control | 2,550 |

EXAMPLE 18

This Example shows the stimulative effect of the compounds of Example 1, Example 16(a) and TeO2 on the induction of IL-2 receptors of human mononuclear cells.

Human MNC were brought to a concentration of $10^6$ cells/ml. RPMI+10% FCS. Aliquots of 0.2 ml. were placed in duplicate wells of microdishes and plates were incubated at 37 C for 24 hrs. Thereafter wells were rinsed twice with RPMI and cells were resuspended with 20 I.U./ml recombinant IL-2 in RPMI and 10% FCS. Plates were further incubated for 48 hrs. and labelled with 3H thymidine 24 hrs. before harvesting.

The proliferation was measured by $^3$HT uptake as described by Gillis et al, J. Immunol. 120,2027 (1978). The results are expressed in counts per minute.

| Test A (μg/ml) | Compound of Ex. 1 | Compound of Ex. 1 | Compound of Ex. 16(a) | TeO2 | Compound of Ex. 16(b) |
|---|---|---|---|---|---|
| 1 | 28625 | 27593 | 21910 | 1563 | 1018 |
| $5 \times 10^{-1}$ | 120755 | 105943 | 145208 | 4667 | 1195 |
| $7 \times 10^{-1}$ | 164538 | 115195 | 130845 | 2475 | 2102 |
| $5 \times 10^{-2}$ | 20022 | 5702 | 8752 | 2515 | 1602 |
| $1 \times 10^{-2}$ | 1952 | 3963 | 9543 | 3108 | 5883 |
| $1 \times 10^{-3}$ | 3652 | 5055 | 6685 | 2867 | 1093 |
| $1 \times 10^{-4}$ | 3558 | 4047 | 6447 | 5540 | 1138 |
| $1 \times 10^{-5}$ | 2474 | 4063 | 8177 | 3442 | 2146 |

(a) Control −2338 (no chemical)
(b) Cell plus recombinant IL-2 (human) Biogen 1.5 × $10^{-6}$ units −3260
(c) Phytohemagglutinin M (Difco) - 195,432

| Test B (μg/ml) | Compound of Ex. 1 | Compound of Ex. 2 | TeO2 | Compound of Ex. 14 |
|---|---|---|---|---|
| 1 | 23488 | 9315 | 3275 | 2620 |
| $5 \times 10^{-1}$ | 66910 | 8688 | 5405 | 2402 |
| $7 \times 10^{-1}$ | 17620 | 5250 | 4302 | 2000 |
| $5 \times 10^{-2}$ | 5390 | 5538 | 4280 | 3290 |
| $1 \times 10^{-2}$ | 6057 | 6418 | 3077 | 3928 |
| $1 \times 10^{-3}$ | 5865 | 5167 | 3800 | 3007 |
| $1 \times 10^{-4}$ | 4960 | 5372 | 2925 | 2327 |
| $1 \times 10^{-5}$ | 7155 | 6397 | 3645 | 2242 |

(a) Control 5573 (no chemical)
(b) Cell plus recombinant IL-2 (human) Biogen 1.5 × $10^{-6}$ units −6858
(c) Phytohemagglutinin M (Difo) - 125,272

EXAMPLE 19

This example shows the stimulative effect of the compounds of the invention on the proliferation of human mononuclear cells.

Human mononuclear cells were obtained by layering heparinized blood over a Ficoll/Hypaque gradient. The mononuclear cells were resuspended in enriched RPMI, rinsed three times and brought to a concentrations of $5 \times 10^5$ cells/ml encriched RPMI. Varying concentrations of the compounds of Ex. 1 and Ex. 2, ranging from 0.005 ug to 5 μg/cell mixture were added to the cells. Aliquots of 0.2 ml of each sample were placed in wells of microplates (triplicates). Microplates were incubated for 72 hours at 37° C. after which they were labelled with $H^3$ methyl-thymidine 1 uCi/well for an additional 24 hours. Cells were then harvested with a cell harvester.

| (μg/ml) | Compound of Ex. 1 | Compound of Ex. 1 |
|---|---|---|
| 1 | 873 | 4700 |
| $5 \times 10^{-1}$ | 18515* | 33700* |
| $1 \times 10^{-1}$ | 2735 | 708 |
| $5 \times 10^{-2}$ | 3865 | 910 |
| $1 \times 10^{-2}$ | 3235 | 1362 |
| $1 \times 10^{-3}$ | 2553 | 2180 |
| $1 \times 10^{-4}$ | 3838 | 2387 |
| $1 \times 10^{-5}$ | 3218 | 2442 |
| control | 2700 | 2943 |

| (μg/ml) | Compound of Ex. 1 | Compound of Ex. 1 | Compound of Ex. 16(a) | TeO$_2$ |
|---|---|---|---|---|
| 5 μg/ml | 5008 | 5182 | 4118 | 3028 |
| 1 μg/ml | 6000 | 5600 | 4557 | 2842 |
| $5 \times 10^{-1}$ | 20488* | 13600* | 18415* | 4773 |
| $1 \times 10^{-1}$ | 7037 | 10382* | 12435* | 4825 |
| $5 \times 10^{-2}$ | 5520 | 5765 | 5953 | 5802 |
| $1 \times 10^{-2}$ | 6898 | 5712 | 6000 | 4730 |
| $1 \times 10^{-3}$ | 5800 | 6000 | 6300 | 6168 |
| $1 \times 10^{-4}$ | 5513 | 6212 | 4587 | 5331 |
| Control | 3600 | 6117 | 6113 | 4912 |

| μg/ml | Compound of Ex. 2 | Compound of Ex. 2 |
|---|---|---|
|  | 4557 | 943 |
| $5 \times 10^{-1}$ | 18415 | 23957* |
| $1 \times 10^{-1}$ | 12435 | 31424* |
| $5 \times 10^{-2}$ | 5953 | 5532 |
| $1 \times 10^{-2}$ | 6000 | 2987 |
| $1 \times 10^{-3}$ | 6300 | 1510 |
| $1 \times 10^{-4}$ | 4321 | 2332 |
| $1 \times 10^{-5}$ | 5118 | 2481 |
| Control | 4587 | 2018 |

*The concentrations that induced proliferation range from $5 \times 10^{-1}$ to $1 \times 10^{-1}$ μg. No significant effect was found for TeO$_2$ at any concentration that was tested.

EXAMPLE 20

Using the procedure of Example 4, human mononuclear cells were tested for their ability to produce IL-2 after induction with PHA or in unstimulated cells from normal donors and from patients suffering from systemic lupus erthyrematous. The IL-2 content was tested according to the procedure of Example 3 using the CTLD IL-2 dependent cell line. The results are reported in Table 5.

TABLE 5

| SUBJECTS | PHA | IL-2 PRODUCTION BY COMPOUND OF EXAMPLE 1 | | | |
|---|---|---|---|---|---|
|  |  | 5 μg 0.2 mlPBS | 1:50 PBS* | 1:100 PBS* | 1:200 PBS* |
| NORMAL |  |  |  |  |  |
| 1 | − | 2.3** | 43.6 | 38.4 | 30.1 |
|  | + | 36.4 | 48.2 | 46.2 | 38.6 |
| 2 | − | 2.1 | 52.2 | 50.3 | 47.1 |
|  | + | 30.4 | 38.9 | 54.2 | 49.8 |
| 3 | − | 2.1 | 50.8 | 46.1 | 31.3 |
|  | + | 38.9 | 53.5 | 44.8 | 38.3 |
| SLE |  |  |  |  |  |
| 1 | − | 2.0 | 37.3 | 32.1 | 26.1 |
|  | + | 6.3 | 24.2 | 19.7 | 15.4 |
| 2 | − | 2.4 | 43.6 | 35.1 | 30.3 |
|  | + | 8.2 | 28.1 | 24.0 | 18.6 |
| 3 | − | 2.4 | 19.2 | 18.1 | 14.4 |
|  | + | 4.1 | 23.8 | 20.2 | 16.8 |

*Dilution of 1 part of 0.2 ml of PBS containing 5 μg of compound of Ex. 1 in 50, 100 or 200 parts of PBS.
**CPM × $10^{-3}$ of $^3$H Thymidine of $5 \times 10^4$ CTLD cells in presence of 1:2 dilution of the supernatants as in Ex. 3.

EXAMPLE 21

This example provides an assay to detect the presence of receptor sites for IL-2. Human mononuclear cells were incubated for 24 hours in the presence of the compound of Example 1 and TeO$_2$. The cells were washed twice with PBS and then incubated with a specific fluoresceinated antibody against IL-2 receptors as described in Uchiyama et al, J. Immunol. 126,1398 (1981) The results were that in the control 2% of the cells were positive; in the presence of PHA 80% of the cells were positive and with 1 μg/ml of the compound of Example 1, 20% of the cells were found to be positive. It was found that TeO$_2$ gave 5% positive cells at a level of 1 μg/ml.

EXAMPLE 22

The effect of the compound of Example 1 on an infection with West Nile virus (WNV) was determined. WNV is a toga virus of the flavivirus group, a positive single stranded RNA virus, which when injected IP to mice usually kills them within 5–8 days as a result of extensive damage to the central nervous system. For this study ICR mice (3 wks of age) were injected IP with the virus at the concentration of $10^3$ or $10^4$ LD 50 units/mouse. Injections of 10 μg/0.2 ml PBS/mouse of the compound of Ex. 1 were given on day −1 (one day prior to injection of virus) and 6 days after injection of virus. Table A shows preliminary results of one such experiment. As can be seen, after 8 days all animals injected with the virus alone died, whereas three out of five animals receiving treatment with the compound of Ex. 1 remained alive.

TABLE A

| Treatment | $10^3$LD$_{50}$ | $10^3$LD$_{50}$ | $10^4$LD$_{50}$ | $10^4$LD$_{50}$ | 0 |
|---|---|---|---|---|---|
| Comp. of Ex. 1 injected | NO | YES | NO | YES | YES |
| # Alive/ Total Animals | 0/6 | 3/5 | 0/6 | 3/5 | 6/6 |

In a second experiment, mice were injected with $10^3$IPLD$_{50}$ virus and received injections of the compound of Example 1 (1 μg/0.2 ml PBS/mouse) on days −1, 1, 2 and 4. Preliminary results of one such experiment on day 8 after injection are shown in Table B. As seen on day 8 all animals injected with virus alone died whereas 3 out of 5 receiving the compound of Ex. 1 remained alive. Two out of the remaining three survived an additional 8 days, whereas the third remained alive without any manifestations of clinical symptoms.

TABLE B

| Treatment | $10^3$IPLD$_{50}$ | $10^3$IPLD$_{50}$ + Compound of Ex. 1 | Compound of Ex. 1 |
|---|---|---|---|
| # Alive/ Total | 0/8 | 3/5 | 5/5 |

EXAMPLE 23

This example shows that the interaction of WNV with cultures of ICR mouse macrophage results in a productive infection. Varying amounts of the compound of Example 1 (5 μg, 1 μg, 0.1 μg) were incubated with a monolayer of mouse macrophages for 24 h. After 24 h macrophages incubated with 5 ug of the compound of Example 1 died whereas others remained unaffected.

All cultures were then infected with 10⁴ PFU/plate. After 72 h incubation the supernatants were collected and the virus was titrated against Vera cells. Table A shows preliminary results of one such experiment. As can be seen, incubation of macrophage cultures with 1 ug of the compound of Example 1 resulted in a 40-fold reduction of virus yield, whereas incubation with 0.1 μg of the compound of Ex. 1 plate resulted in a ten-fold reduction in virus yield.

TABLE A

| Treatment | Virus Yield (PFU/ml) |
|---|---|
| Control (virus alone) | $2 \times 10^4$/ml |
| Compound of Example 1 μg/plate | $5 \times 10^2$/ml |
| Compound of Example 1 0.1 μg/plate | $2 \times 10^3$/ml |

We claim:

1. A method for stimulating cells to produce lymphokines, said method comprising contacting lymphokine producing cells with an amount of a compound of the formula:

or or

TeO₂ or

PhTeCl₃ wherein Q is Te or Se; t is 1 or 0; u is 1 or 0; v is 1 or 0; R, R₁, R₂, R₃, R₄, R₅, R₆, R₇, R₈ and R₉ are the same or different and are independently selected from the group consisting of hydrogen, hydroxyalkyl of 1 to 5 carbons, hydroxy, alkyl of from 1 to 5 carbon atoms, halogen, haloalkyl of 1 to 5 carbon atoms, carboxy, alkylcarbonylalkyl of 2 to 10 carbons, alkanoyloxy of 1 to 5 carbon atoms, carboxyalkyl of 1 to 5 carbon atoms, acyl, amido, cyano, amidoalkyl of 1 to 5 carbons, N-monoalkylamidoalkyl of 2 to 10 carbons, N,N-dialkylamidoalkyl of 4 to 10 carbons, cyanoalkyl of 1 to 5 carbons, alkoxy of 1 to 5 carbon atoms, alkoxyalkyl of 2 to 10 carbon atoms and —COR₁₀ wherein R₁₀ is alkyl of from 1 to 5 carbons; which will stimulate said lymphokine producing cells to produce increased quantities of lymphokines.

2. A method for stimulating cells to produce lymphokines as defined in claim 1 wherein the compound of the formula:

wherein X is halogen.

3. A method for stimulating cells to produce lymphokines as defined in claim 1 wherein X is chloro.

4. A method for stimulating cells to produce lymphokines as defined in claim 1 wherein the compound is of the formula:

wherein X is halogen.

5. A method for stimulating cells to produce lymphokines as defined in claim 1 wherein X is chloro.

6. A method for stimulating cells to produce lymphokines as defined in claim 1 wherein the compound is of the formula TeO₂.

7. A method for stimulating cells to produce lymphokines as defined in claim 1 wherein the compound is Ph Te Cl₃.

* * * * *